(12) United States Patent
Dobler et al.

(10) Patent No.: US 8,985,479 B2
(45) Date of Patent: Mar. 24, 2015

(54) FRAMED FRESHENER

(75) Inventors: Sven Dobler, Huntington, NY (US);
Aaron R. Bauhs, New York, NY (US);
Ahmed R. Alai-Tafti, Smithtown, NY (US); Jonathan Millen, Melville, NY (US)

(73) Assignee: Oplandi, Inc., Farminigton, NY (US)

( * ) Notice: Subject to any disclaimer, the term of this patent is extended or adjusted under 35 U.S.C. 154(b) by 1423 days.

(21) Appl. No.: 12/290,815

(22) Filed: Nov. 4, 2008

(65) Prior Publication Data

US 2009/0123344 A1    May 14, 2009

Related U.S. Application Data

(60) Provisional application No. 61/002,690, filed on Nov. 9, 2007.

(51) Int. Cl.
*A24F 25/00* (2006.01)
*A61L 9/04* (2006.01)
*A61L 9/12* (2006.01)

(52) U.S. Cl.
CPC .. *A61L 9/048* (2013.01); *A61L 9/12* (2013.01)
USPC .............. 239/56; 239/55; 239/54; 239/34; 239/289; 40/725

(58) Field of Classification Search
USPC ................. 239/34–60, 289; 40/723, 725
See application file for complete search history.

(56) References Cited

U.S. PATENT DOCUMENTS

| | | | | |
|---|---|---|---|---|
| 1,775,784 A | * | 9/1930 | Peters | 40/124.5 |
| 2,577,320 A | * | 12/1951 | Fenyo | 239/55 |
| 5,304,358 A | * | 4/1994 | Hoyt et al. | 422/305 |
| 5,361,522 A | * | 11/1994 | Green | 40/725 |
| 2004/0169091 A1 | * | 9/2004 | Wheatley et al. | 239/6 |
| 2006/0000920 A1 | * | 1/2006 | Leonard | 239/34 |

* cited by examiner

*Primary Examiner* — Dinh Q Nguyen
(74) *Attorney, Agent, or Firm* — Paul M Denk

(57) ABSTRACT

A framed freshener provides a thermal formed cavity, or thermoplastic shell, carrying scented gel that fits into a picture frame. The present invention locates a fragrant gel in a thermal formed cavity or thermoplastic shell or container which is then placed within a suitably designed picture frame. Coupling a fragrance with a photo in a frame, the present invention seeks to foster memories in those who view the frame. Additionally, the shell carrying gel makes the frame a decorative air freshening device. The picture frame and the opening for the fragrance container can be die cut to any shape. An alternate embodiment has the shell supported in a wire frame upon a base.

3 Claims, 3 Drawing Sheets

FRAMED FRESHENER

CROSS-REFERENCE TO RELATED APPLICATIONS

This non-provisional patent application claims priority to the provisional patent application having Ser. No. 61/002,690, which was filed on Nov. 9, 2007.

BACKGROUND OF THE INVENTION

The framed freshener generally relates to air freshening devices and more specifically to a picture frame with an integral scented gel.

A variety of gel products are on the market, used mostly for toys, novelty, gifts, window clings, and decorative ornaments. The consumers are particularly attracted by the gel products due to their features of softness, color, and introduction of a scent or fragrance. These features, desired by consumers, are related to the nature of the gel product, which may contain mineral oil. Additionally, the careful selection of the composition of gel products has related the good dispersion between a scent or fragrance and the surface of the gel products for introduction into the atmosphere.

After setting a scented liquid into a thermal form cavity and forming a gel in a desired shape with the scent within its composition, a frame having a decorated surface and edge treatment includes the gel within the thermal form in an opening, aperture, or other space adjacent to other openings for mounting a photo or the like. The gel adjacent to a photo in a frame can then be located where suitable in a home or office.

Conventional picture frames typically consist of elongated members of wood, metal, or plastic arranged in a rectangular shape with the corners connected with adhesives or mechanical fasteners. The display photo is placed in the frame along with a transparent front panel of glass or plastic, matting if desired, and backing materials, which are further attached with more fasteners, and positioned behind the photo or artwork within the elongated members shaped into a frame, often rectangular but other shapes are possible. Particularly, the frame has a wire, or other suitable fastener appropriately secured, for use in hanging the picture on a wall or other vertical surface. Alternatively, the frame has a stand for supporting a picture upright upon a flat surface such as a shelf, table, or desk.

DESCRIPTION OF THE PRIOR ART

Some prior art patents relate to the use of gels related to picture frames. One is U.S. Pat. No. 6,395,125, upon the process for making a picture frame. The picture frame has a border printed upon the perimeter of transparent sheet material and then cut from the sheet. The border and a transparent window sheet are then adhered together upon a polymer sheet extending beyond the border. The polymer sheet is then folded behind the window and cut to provide a leg to hold the picture frame upright. A photo or other display is placed within the window. The polymer laminated picture frame though lacks the ability to provide a fragrance therefrom.

Then the U.S. Pat. No. 5,916,650, shows a removable display cover and method. This cover has a border printed upon a plastic sheet with a transparent window generally in the center of the cover. The cover has magnetic, static charge, or surface tension that sticks the cover to another surface. The cover is placed over a photo or other display, securing the photo upon the surface. This cover also does not provide a fragrance.

The present invention overcomes the disadvantages of the prior art and provides a fragrance carrying material within a picture frame. The framed freshener provides scent wherever the frame is located in a home, office, or other location. The fragrance may trigger stronger memories in cooperation with a photograph or other item displayed within the frame of the present invention.

SUMMARY OF THE INVENTION

Generally, the present invention of a framed freshener provides a thermal formed cavity holding a scented gel that fits into a picture frame. The sense of smell has been known to trigger long dormant memories. Coupling a certain fragrance with a photo or other item in a frame, the present invention seeks to foster memories in those who view the frame. Additionally, the thermal formed cavity holding a scented gel makes the frame holding it into a concealed, or unobtrusive, air freshening device. The present invention locates a fragrance source in a container, such as a thermal formed cavity or thermoplastic shell, and places the container in a suitably designed picture frame. The picture frame and the opening for the fragrance container can be die cut to a specific shape.

There has thus been outlined, rather broadly, the more important features of the invention in order that the detailed description thereof that follows may be better understood and that the present contribution to the art may be better appreciated. The present invention also includes a gel composition, a tab on the shell, round, ovoid, irregular, rectangular and square shaped shells, a flange upon the perimeter of the shell for securement upon the matting of a frame, and a perforated die and a lid to control the release of fragrance from the invention and to prevent spillage. Additional features of the invention will be described hereinafter and which will form the subject matter of the claims attached.

Numerous objects, features and advantages of the present invention will be readily apparent to those of ordinary skill in the art upon a reading of the following detailed description of the presently preferred, but nonetheless illustrative, embodiment of the present invention when taken in conjunction with the accompanying drawings. Before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, the phraseology and terminology employed herein are for the purpose of description and should not be regarded as limiting.

One object of the present invention is to provide a framed freshener with an improved scented gel in a thermal formed cavity, or thermoplastic shell, that is then mounted into a picture frame.

Another object is to provide such a framed freshener with a scented gel that is flexible and removable from the picture frame.

Another object is to provide such a framed freshener within a picture frame that has an arrangement or design upon the surface of the thermal formed cavity, thermoplastic shell, or resulting gel by die cutting, molding, or other shape imposing methods.

Another object is to provide such a framed freshener with a scented gel that releases scent without electric or mechanical means.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated a preferred embodiment of the invention.

BRIEF DESCRIPTION OF THE DRAWINGS

In referring to the drawings.

The same reference numerals refer to the same parts throughout the various figures.

DESCRIPTION OF THE PREFERRED EMBODIMENT

Figure 1:
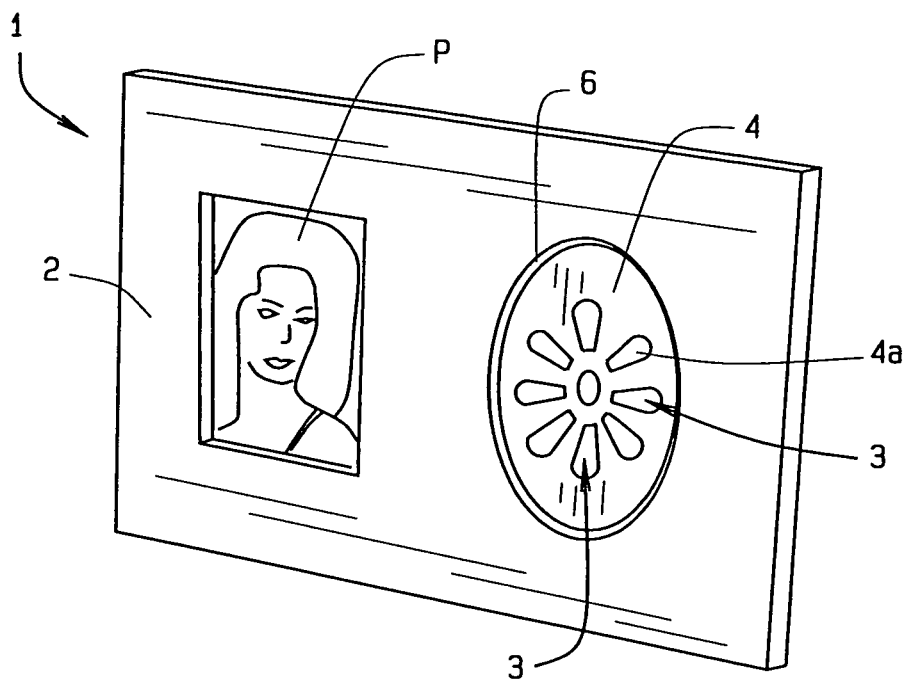
FIG. 1 shows a perspective view of the present invention.

The present art overcomes the prior art limitations by providing a framed freshener 1 in FIG. 1 that has a picture frame 2 that provides a scent, fragrance, or freshener suitable for locating in a person's home or office as desired. The scent is provided from a gel 3 contained within a shell 4 and the shell is then placed within the picture frame. The gel is placed within the shell or container in liquid form and then sets to its final consistency in less than five minutes.

More particularly, the framed freshener has the gel 3 contained within a shell 4 or other thermal formed shell or cavity. The gel releases scents through perforated openings 4a—also called lidding—in the shell, or container, and its own surfaces. Here the openings are shown in a flower petal like arrangement though other arrangements are possible. The shell is placed upon the rear of the frame 2 at an aperture 5 with an edge treatment 6 here shown as a bevel though other edge treatments are possible. In this embodiment, the shell is located and spaced apart from another picture P placed within the frame.

In further description, the gel 3 comprises a polymer, oil, and the like blended in liquid form. The gel is then pored into a thermal formed plastic shell container as opposed to a free standing form. The gel then attains any one of a variety of shapes, here the present invention has an ovoid shape, though rectangular and square are likely alternate shapes. The polymeric gel retains its features over time: flexibility, scent transmission rate, and color among others. The gels of the present invention are generally translucent, and preferably transparent, while remaining receptive to color dyes.

The composition of the present invention blends a mixture of polymers in combination with hydrocarbon oil to form a gel. The hydrocarbon oil can be, for example, a paraffinic oil, a naphthenic oil or a mineral oil. The hydrocarbon oils contain a fragrance that releases over time, in the present invention, for at least 96 hours. The present invention does not use electric resistance heat or mechanical ventilation to release the fragrance. The fragrance or scent naturally escapes the gel at a known rate subject to atmospheric conditions at the location of the framed freshener. The fragrance generally has a positive smell and can include flower based smells, spice based smells, pleasant organic materials, and the like. Low molecular weight polyalphaolefin maintains the rigidity of the gel while highly branched alpha olefin polymers bind the oil and increase the hardness of the gel. In the preferred embodiment, the gel has a translucent quality with a hint of color. Gels attain a color through dyeing, preferably an oil soluble dye. The color coordinates with that of the picture frame and the taste of the user of the invention.

In an alternate embodiment, generally for children, luminescent, fluorescent, pearlescent particles, glitters, metallic pigments, and optical brightener additives mixed into the gel preferably and upon the frame or thermoformed container alternatively, add a degree of fun to the invention. These additives provide shine, sparkling, and illumination of the gel or frame in darkness. Other useful additives are a light absorber to lengthen shelf stability of the gel and the picture frame when exposed to visible or ultraviolet light. If desired, thermochromic pigments may be added to the frame or the thermoformed plastic shell that change color at predetermined temperatures.

Mineral oils are highly refined, colorless, and odorless petroleum oils. A preferred mineral oil to mix with the polymers of the invention is "white" mineral oil. White mineral oil is generally recognized as safe for contact with human skin because people may touch the gel or its shell from time to time. Mineral oil may be characterized in terms of its density and viscosity, where light mineral oil is relatively less viscous than heavy mineral oil. The mineral oil of the present invention includes amounts ranging from about 5 to about 30% by weight, and preferably from about 10 to about 20% by weight.

Figure 2:
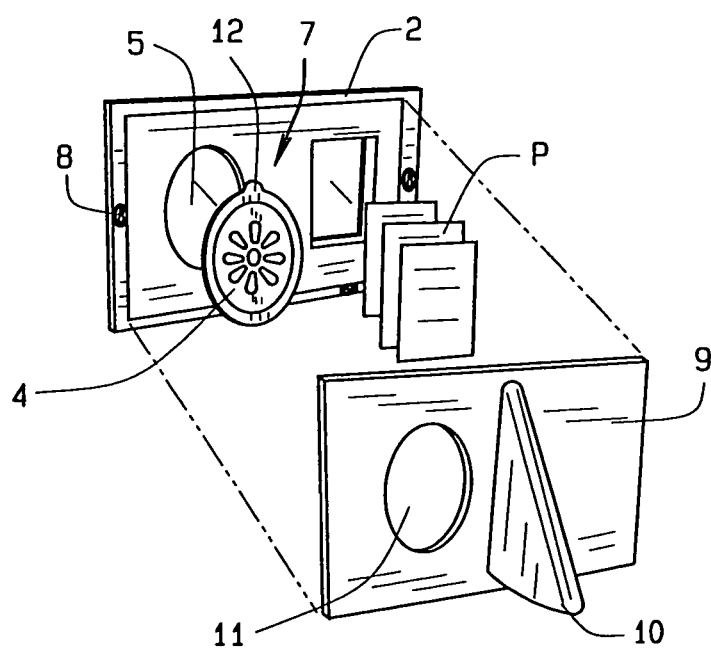
FIG. 2 describes an exploded view of the present invention from the rear.

The framed freshener 1 assembles from components shown in FIG. 2. Here, the frame 2 has a generally rectangular shape with the rear surface 7 in view. The rear surface has a plurality of clips 8 spaced near the perimeter, with a minimum of one clip though three are shown. The clips rotate from the frame upon a backing 9. The backing is also rectangular though of slightly less extent than the frame 2 so the backing fits within the perimeter of the frame. The backing has a stand 10 that unfolds, generally perpendicular to the frame that supports the frame upright in this embodiment as previously shown in FIG. 1. The backing also has an aperture 11 of similar proportions to the shell 4 and slightly less than the proportions of the aperture 5 in the frame. The aperture 11 of the backing and the aperture 5 of the frame cooperate for ready release of scent from the gel 3 within the shell 4. The scent can disperse from the front and the rear of the frame 2.

The present invention assembles by placing the shell 4 into the aperture 5 with a flange 12 extending from the shell located towards the rear surface 7. The flange has greater width and length than the apertures 5, 11 so that the shell does not fall through the frame 2 and remains within the framed freshener 1. A photo is then placed in another opening in the frame as desired. Then the backing 9 is placed upon the rear surface 7, the shell 4, and the photo P with the stand 10 positioned to open and then support the frame 2 upright. The clips 8 are turned with a portion behind the backing, thus securing the frame 2, shell 4, and photo P to the backing 9. Additionally, the flange has a tab extending perpendicular therefrom to ease grasping of the shell for insertion into the aperture 5 by a person.

Figure 3:
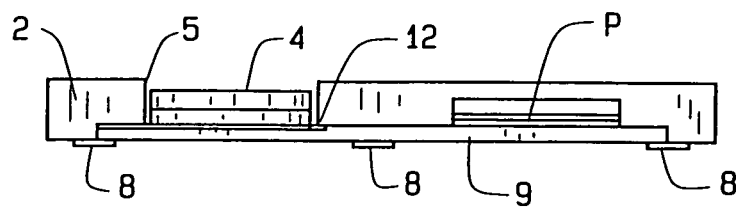
FIG. 3 is a top sectional view of the present invention.

FIG. 3 illustrates a top, sectional view of the assembled framed freshener 1 with the stand folded. The clips 8 are turned so the backing 9 is pressed into the rear surface 7 of the frame 2. In front of the backing, the shell 4 fits within the aperture 5 of the frame 2. The shell remains within the frame as the flange 12 remains between the backing and the frame proximate the perimeter of the aperture 5. The flange generally extends around the perimeter of the shell and is made from the same material as the shell. The flange generally suspends the shell within the apertures 5, 11 for free flow of scent. To the side of the shell, or container, the present invention has a photo P in the other opening of the frame 2. The photo is located within the backing, matting, and the frame. The backing extends across the back of the photo and matting, thus preventing the photo from falling out of the frame.

Figure 4:
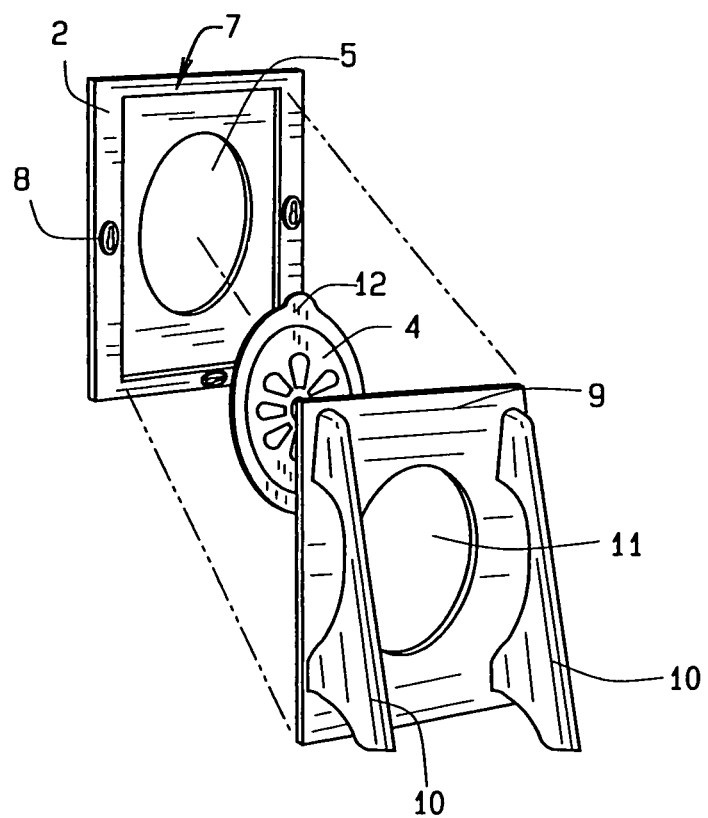
FIG. 4 describes an exploded view of an alternate embodiment of the present invention; and, FIG. 5 describes a front view of an alternate embodiment.

An alternate embodiment of the invention appears in FIG. 4 that has just the shell and no separate photo. As before, the frame 2 has a rear surface 7 with an aperture 5 and a plurality of clips 8 located upon the perimeter of the frame. The aperture 5 has an edge condition and admits the shell 4, or other thermal formed cavity or container, into the aperture. The shell contains the gel 3 with a fragrance that is released through openings in the shell. A perimeter flange 12 upon the shell secures it within the frame as before. A backing 9 secures upon the shell and within the rear surface of the frame and under the clips 8. This embodiment has two stands 10 that unfold oppositely from the backing. The stands in cooperation with the frame provide three contacts with a supporting surface so the frame remains upright. The backing has an aperture 11 that also permits free flow of scent from the shell or container. In assembly, the flange 12 of the shell is located between the frame and the backing so that the shell is suspended within the apertures 5, 11.

Figure 5:
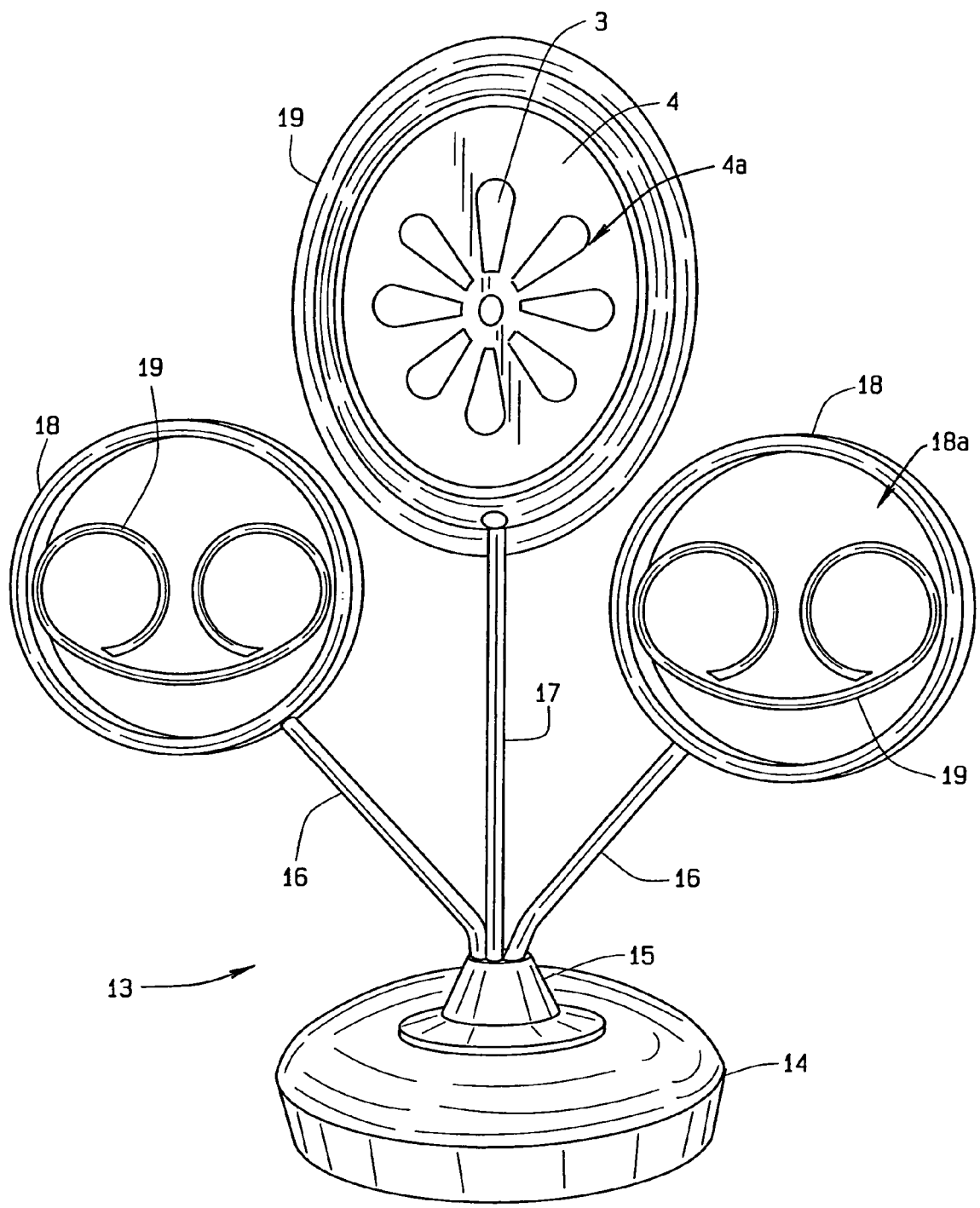

Another alternate embodiment takes form in FIG. 5 that has a shell 4 as one component in a stand 13. The stand has a base 14, generally round, with a raised central fitting 15 that receives three stems. Two stems are lateral stems 16 that extend upwardly and outwardly from the central fitting. The third stem is an upright stem 17 that extends generally perpendicular to the base. The stems 16, 17 are generally cylindrical of narrow diameter. The lateral stems terminate in a ring 8 with an internal spring retainer 19. The retainer engages an inner rim 18a and stays within the ring. The retainer can support a photo or other item within the ring 18 or be used alone. Now the upright stem terminates opposite the base with an oval frame 19. The upright stem 17 attaches to the oval frame at the end of the major axis. The oval frame contains the shell 4 within. As before, the shell 4 has a plurality of openings 4a that admit scent from a gel 3 contained therein. As the oval frame is hollow, the shell can release scent from opening upon both sides of the shell. Here the openings 4a have a flower like arrangement though other shapes are possible. This embodiment places the framed freshener high above the base 14 to maximize dispersion of the scent from the gel.

From the aforementioned description, a framed freshener has been described. The device is uniquely capable of providing a fragrance or scent from a picture frame wherever the frame is located. The fragrance comes from a gel contained within a thermoplastic shell, cavity, or container, placed within a picture frame. The framed freshener and its various components may be manufactured from many materials, including but not limited to, wood, steel, aluminum, polymers, polyvinyl chloride, high density polyethylene, polypropylene, ferrous and non-ferrous metals, their alloys, and composites, and the gel may include the various ingredients as described above and the like.

As such, those skilled in the art will appreciate that the conception, upon which this disclosure is based, may readily be utilized as a basis for the designing of other structures, methods and systems for carrying out the several purposes of the present invention. Therefore, the claims include such equivalent constructions insofar as they do not depart from the spirit and the scope of the present invention.

We claim:

1. A decorative device for dispensing a freshening scent into a room, comprising:
    a frame having at least one aperture therethrough and a means for supporting said frame upright;
    a container, said container occupying said at least one aperture;
    a gel located within said container, said gel comprising one or more polymers and an oil, and a freshening scent therein released over time;
    said container having a flange at least partially along the perimeter of said container, said flange generally perpendicular to said container; and
    perforated lidding upon said container preventing spillage of said gel and controlling release of fragrance therefrom.

2. A decorative device for dispensing a freshening scent into a room, comprising:
    a frame having at least one aperture therethrough and a means for supporting said frame upright;
    a container, said container occupying said at least one aperture;
    a gel locating within said container, said gel comprising one or more polymers and an oil, and a freshening scent therein released over time; and
    said container exposes the gel directly to the atmosphere on at least one vertical surface.

3. A decorative device for dispensing a freshening scent into a room, comprising:
    a frame having at least one aperture therethrough and a means for supporting said frame upright;
    a container, said container occupying said at least one aperture;
    a gel locating within said container, said gel comprising one or more polymers and an oil, and a freshening scent therein released over time; and
    the gel comprises at least one vertical surface exposed directly to the atmosphere.

* * * * *

UNITED STATES PATENT AND TRADEMARK OFFICE
CERTIFICATE OF CORRECTION

PATENT NO.        : 8,985,479 B2
APPLICATION NO.   : 12/290815
DATED             : March 24, 2015
INVENTOR(S)       : Sven Dobler et al.

It is certified that error appears in the above-identified patent and that said Letters Patent is hereby corrected as shown below:

On the Title page, item (73)

Incorrect:
Assignee: Oplandi, Inc., Farminigton, NY (US)

Correct:
Assignee: Orlandi, Inc., Farmingdale, NY (US)

Signed and Sealed this
Ninth Day of June, 2015

Michelle K. Lee
*Director of the United States Patent and Trademark Office*